United States Patent [19]

Michaels

[11] Patent Number: 5,185,148

[45] Date of Patent: * Feb. 9, 1993

[54] **PROCESS FOR CONTROLLING SCARAB PESTS WITH *BACILLUS THURINGIENSIS* ISOLATES**

[75] Inventor: Tracy E. Michaels, Escondido, Calif.

[73] Assignee: Mycogen Corporation, San Diego, Calif.

[*] Notice: The portion of the term of this patent subsequent to Oct. 30, 2007 has been disclaimed.

[21] Appl. No.: 828,430

[22] Filed: Jan. 30, 1992

Related U.S. Application Data

[63] Continuation-in-part of Ser. No. 808,316, Dec. 16, 1991, abandoned.

[51] Int. Cl.⁵ ............................................ A01N 63/00
[52] U.S. Cl. ............................... 424/93 L; 435/252.5; 435/832
[58] Field of Search .................. 424/93 L; 435/252.5, 435/832

[56] References Cited

U.S. PATENT DOCUMENTS 4,996,765 10/1990 Payne et al. ..................... 424/93 L

FOREIGN PATENT DOCUMENTS 0202739 3/1986 European Pat. Off. .

OTHER PUBLICATIONS

Couch, T. L. (1980) "Mosquito Pathogenicity of *Bacillus thuringiensis* var. *israelensis*," Developments in Industrial Microbiology 22:61–76.

Beegle, C. C., (1978) "Use of Entomogenous Bacteria in Agroecosystems," Developments in Industrial Microbiology 20:97–104.

Krieg, Von A., A. M. Huger, G. A. Langenbruch and W. Schnetter, (1983) "*Bacillus thuringiensis* var. *tenebrionis*: ein neuer, gegenuber Larven von Coleopteren wirksamer Pathotyp", Zeitschrift fur angewandte Entomologie (Journal of Applied Entomology) 96:500–508.

Primary Examiner—Douglas W. Robinson
Assistant Examiner—Jean C. Witz
Attorney, Agent, or Firm—Saliwanchik & Saliwanchik

[57] ABSTRACT

Certain isolates of *Bacillus thuringiensis* (*B.t.*) have been found to have activity against Scarab pests. These isolates are designated *B.t.* PS86B1, *B.t.* PS43F and *B.t.* PS50C. These isolates, or transformed hosts containing the gene expressing a Scarab-active toxin obtained from the isolates, can be used to control Scarab-active pests, e.g., Masked Chafer, *Cyclocephala* sp., June Beetle, *Cotinis* sp., Northern Masked Chafer, *Cyclocephala borealis*, Japanese Beetle, *Popillia japonica*, and Pasedena Masked Chafer, *Cyclocephala pasadenae*, in various environments.

12 Claims, No Drawings

PROCESS FOR CONTROLLING SCARAB PESTS WITH *BACILLUS THURINGIENSIS* ISOLATES

CROSS-REFERENCE TO A RELATED APPLICATION

This is a continuation-in-part of co-pending application Ser. No. 07/808,316, filed on Dec. 16, 1991, abandoned.

BACKGROUND OF THE INVENTION

*Bacillus thuringiensis* (*B.t.*) produces an insect toxin designated as δ-endotoxin. It is synthesized by the *B.t.* sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of *B.t.* covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. *israelensis*," Developments in Industrial Microbiology 22:61–76; Beegle, C. C., (1978) "Use of Entomogenous Bacteria in Agroecosystems," Developments in Industrial Microbiology 20:97–104. Krieg, et al., Z. ang. Ent. (1983) 96:500–508, describe a *B.t.* isolate named *Bacillus thuringiensis* var. *tenebrionis*, which is reportedly active against two beetles in the order Coleoptera. These are the colorado potato beetle, *Leptinotarsa decemlineata*, and *Agelastica alni.*

In European Patent Application 0 202 739 there is disclosed a novel *B.t.* isolate active against Coleoptera. It is known as *B. thuringiensis* var. *san diego* (*B.t.sd.*). U.S. Pat. No. 4,966,765 discloses the coleopteran-active *Bacillus thuringiensis* isolate *B.t.* PS86B1.

Insects in the family Scarabaeidae (Scarabs) constitute a serious pest control problem, especially when destructive larval stage insects infest high value turf found in golf courses, playing fields and lawns. The larvae of many species also attack grains, tuberous crops, and ornamentals. Larvae are called "white grubs" or "chafer grubs" and can be found in decaying organic matter (rotting leaves, manure, etc.) or 2–10 cm. deep in soil where they consume the plant roots. In turf infested areas there can be as many as 30 grubs per square foot. The damage caused by an infestation becomes most apparent in the fall when the third instar grubs are feeding. Adult beetles of some Scarab species will feed on a wide variety of vegetative host, damaging foliage, fruit and flowers of woody and herbaceous plants. In the U.S. and Europe, populations of larvae and adults have developed resistance to chemical insecticides such as the organochlorines and DDT.

Several Scarab pests are of economic importance. Particularly important pests in the U.S., especially east of the Rockies, but also in the Western States, are the Masked Chafers, *Cyclocephala* sp. In the east, the Northern Masked Chafer, *C. borealis*, and the Southern Masked Chafer, *C. immaculata*, are common pests, while in California *C. hirta* and *C. pasadenae* are present. Also, in the U.S., especially in the area east of the rockies, infestations of Japanese beetles *Popillia* sp., May or June beetles *Phyllophaga* sp., black turfgrass beetles *Ataenius* sp., European chafers *Rhizotrogus* sp. tend to necessitate the greatest amount of insecticide treatments. Other important Scarab pests in the U.S. can be quite damaging but localized such as with Oriental beetles *Anomala* sp., hoplia chafers *Hoplia* sp., green June beetle *Cotinis* sp., and Asiatic garden beetles *Maladera* sp. Several Scarabs not present the U.S., are of economic importance in Europe including rose chafers *Cetonia* sp., cockchafers *Melolontha* sp., flower beetles *Adoretus* sp., and garden chafers *Phyllopertha* sp. The green June beetles, *Cotinis* sp., can cause serious damage where populations become abundant. The adults are attracted to ripening fruit and will devour figs, peaches and other thin skinned fruit while on the tree. Larvae are attracted to decaying organic matter and most commonly become pests in turf or fields which have been fertilized with manure. The feeding and tunnelling of the large larvae can become disruptive. The Eastern Green June Beetle *Cotinis nitida* is present in the midwestern and eastern states, while the Green June Beetle *C. mutabilis* occurs in many of the western states.

BRIEF SUMMARY OF THE INVENTION

The subject invention concerns the discovery that certain *Bacillus thuringiensis* (*B.t.*) isolates are active against Scarab pests. More specifically, the invention concerns the use of *B.t.* PS86B1 (NRRL B–18299), *B.t.* PS50C (NRRL B–18746), *B.t.* PS43F (NRRL B–18298), and microbial hosts transformed with the gene expressing a Scarab-active toxin obtained from those isolates, to control Scarab pests.

The subject invention also includes mutants of *B.t.* PS86B1, PS50C and *B.t.* PS43F, which have substantially the same pesticidal properties as the parent *B.t.* microbe. Procedures for making mutants are well known in the microbiological art. Ultraviolet light and nitrosoguanidine are used extensively toward this end.

Further, the invention also includes the treatment of substantially intact *B.t.* cells, and recombinant cells containing a gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

DETAILED DISCLOSURE OF THE INVENTION

The cultures disclosed in this application are on deposit in the Agricultural Research Service Patent Culture collection (NRRL), Northern Regional Research Center, 1815 North University Street, Peoria, Ill. 61604, USA. *B.t.* PS86B1 (NRRL B–18299) is disclosed in U.S. Pat. No. 4,966,765. *B.t.* PS43F (NRRL B–18298) is disclosed in U.S. Pat. No. 4,996,155. *B.t.* PS50C (NRRL B–18746) was deposited under the provisions of the Budapest Treaty for the Depositing of Microorganisms. *B.t.* PS50C has the following characteristics in its biologically pure form:

Characteristics of *B.t.* PS50C

Colony morphology—Large colony, dull surface, typical *B.t.*

Vegetative cell morphology—typical *B.t.*

Culture methods—typical for *B.t.*

Flagellar serotyping—PS50C belongs to serotype 18, kumamotoensis.

Crystal morphology—a sphere.

RFLP analysis—Southern hybridization of total DNA distinguishes *B.t.* PS50C from *B.t.sd.* and other *B.t.* isolates.

Alkali-soluble proteins—SDS polyacrylamide gel electrophoresis (SDS-PAGE) shows a 130 kDa doublet protein.

A comparison of the characteristics of *B. thuringiensis* PS50C (*B.t.* PS50C) to the characteristics of the known *B.t.* strains *B. thuringiensis* var. *san diego* (*B.t.sd.*), *B. thuringiensis* PS86B1 (NRRL B-18299), and *B. thuringiensis* var. *kurstaki* (HD-1) is shown in Table 1.

TABLE 1

| Comparison of B.t. PS50C, B.t. PS86B1, B.t.sd., and B.t. HD-1 | | | | |
|---|---|---|---|---|
| | B.t. PS50C | B.t.sd. | B.t. PS86B1 | B.t. HD-1 |
| Serovar | kumamotoensis | morrisoni | tolworthi | kurstaki |
| Type of inclusion | sphere | square wafer | flat, pointed ellipse, plus sm. inclusions | Bipyramid |
| Size of alkali soluble proteins by SDS-PAGE | 130 kDa doublet | 72,000 64,000 | 75,000 68,000 61,000 | 130,000 68,000 |
| Host range | Coleoptera | Coleoptera | Coleoptera | Lepidoptera |

The *B.t.* microbes of the invention, can be cultured using standard art media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

The *B.t.* pesticide of the invention can be applied to the soil to control Scarab larvae as follows:
  a granule to the soil
  a granule mixed with sand, which fills holes during aeration of turf
  a granule with a sub-surface applicator upon re-seeding in turf
  a spray to the soil (soil drench)
  a spray following aeration
  a spray applied with sub-surface applicator
  combined with a water holding polymer placed in soil with a sub-surface applicator

*B.t.* pesticidal treatment for adult scarab pests can be done as follows:
  granules with attractant, dispersed in area where beetles are flying
  attractant bait where beetles can congregate to feed
  as a foliar spray to host plant The *B.t.* microbes can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

Toxin genes are obtainable from the Scarab-active *B. thuringiensis* (*B.t.*) isolates by well known art procedures.

These genes of can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of Scarab pests where they will proliferate and be ingested by the pests. The result is a control of the unwanted pests. Alternatively, the microbe hosting the toxin gene can be treated under conditions that prolong the activity of the toxin produced in the cell. The treated cell then can be applied to the environment of target pests. The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes eu.rophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretori-*

*ensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop condon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* sp., *Aureobasidium* sp., *Saccharomyces* sp., and *Sporobolomyces* sp.; phylloplane organisms such as *Pseudomonas* sp., *Erwinia* sp. and *Flavobacterium* sp.; or such other organisms as *Escherichia, Lactobacillus* sp., *Bacillus* sp., *Streptomyces* sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans,* and the like.

The cell will usually be intact and be substantially in the proliferative form when treated, rather than in a spore form, although in some instances spores may be employed.

Treatment of the recombinant microbial cell can be done as disclosed infra. The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation of killing retains at least a substantial portion of the bioavailability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like), The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the Scarab pests, e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* Isolates and Transformed hosts

A subculture of the *B.t.* isolates and transformed hosts of the invention can be used to inoculate the following medium, a peptone, glucose, salts medium.

| Bacto Peptone | 7.5 g/l |
| --- | --- |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and crystals, obtained in the above fermentation, can be isolated by procedures well known in the art. A frequently-used procedure is to subject the harvested fermentation broth to separation techniques, e.g., centrifugation.

EXAMPLE 2

Testing of *B.t.* PS86B1 and Transformed Hosts

Third instar Pasadena Masked Chafers, Cyclocephala pasadenae, were found to be susceptible to the *B.t.* isolate PS86B1 as well as a *Pseudomonas fluorescens* transformed host containing the δ-endotoxin expressing gene obtained from *B.t.* PS43F. In the bioassays, larvae were fed an aqueous suspension of the material mixed with ryegrass roots. Larvae were held with the treated diet at room temperature in 1 oz. plastic cups, and observed for mortality by prodding. Dosages of PS86B1 and the *Pseudomonas fluorescens* transformed host greater than 500 ppm (δ-endotoxin protein/diet) gave 80% control in 15 days.

EXAMPLE 3

Testing of *B.t.* Transformed Host Containing the δ-Endotoxin Gene from PS50C

The transformed host was prepared by introducing plasmid pMYC1638 (NRRL B-18751), containing the δ-endotoxin expressing gene obtained from *B.t.* PS50C, into an acrystalliferous (cry⁻) *B.t.* host (HD-1 cryB obtained from A. Aronson, Purdue University) by standard electroporation procedures.

Larvae of *Cotinis sp.* were found to be susceptible to the transformed host containing the δ-endotoxin expressing gene obtained from the *B.t.* isolate PS50C. The larvae were fed an aqueous suspension of the transformed host mixed with peat moss. The larvae were held at room temperature in 1 oxz. plastic cups with the treated peat, and checked regularly during the assays for mortality. Dosages of the transformed host of 750 ppm (δ-endotoxin/diet) caused 90% mortality of the larvae by day 13. In addition, the transformed host was shown to affect all three instar stages of the larvae.

EXAMPLE 4

Testing of *B.t.* PS86B1 Against *Cyclocephala borealis*

Third instar Northern Masked Chafer *Cyclocephala borealis* were found to be susceptible to the *B.t.* isolate PS86B1. Larvae were fed Kentucky bluegrass roots which had been dipped in a *B.t.* suspension. Larvae were held at room temperature in 1 oz. cups containing the treated roots and observed for mortality by prodding. Dosages greater than 500 ppm (protein/diet) gave 79% control in 7 days.

EXAMPLE 5

Testing of *B.t.* PS86B1 against *Popillia japonica*

Third instar Japanese beetle *Popillia japonica* were found to be susceptible to the *B.t.* isolate PS86B1. Larvae were fed a *B.t.* suspension mixed with compost. Larvae were held with the treated compost at room temperature in 1 oz. plastic cups and observed for mortality by prodding. Dosages of PS86B1 greater than 500 ppm (protein/diet) gave greater than 40% control in 7 days.

EXAMPLE 6

Insertion of Toxin Gene Into Plants

The genes coding for the pesticidal toxin, as disclosed herein, can be inserted into plant cells using the Ti plasmid from *Agrobacter tumefaciens*. Plant cells can then be caused to regenerte into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 7

Cloning of *B. thuringiensis* Genes Into Baculoviruses

The genes of the invention can be cloned into baculoviruses such as *Autographa californica* nuclear polyhedrosis virus (AcNPV). Plasmids can be constructed that contain the AcNPV genome cloned into a commercial cloning vector such a pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

I claim:

1. A process for controlling Scarab pests which comprises contacting said pests, or the environment of said pest, with a Scarab-controlling effective amount of a *Bacillus thuringiensis* isolate "having all of the identifying characteristics of an isolate" selected from the group consisting of *Bacillus thuringiensis* PS86B1, *Bacillus thuringiensis* PS43F, and *Bacillus thuringiensis* PS50C, spores or toxin crystals, thereof or Scarab active mutants thereof "which retain the parent microbe activity against scarab pests".

2. The process, according to claim 1, wherein said pest is contacted with a scarab-controlling sufficient amount of a *Bacillus thuringiensis* isolate selected from the group consisting of *Bacillus thuringiensis* PS86B1, *Bacillus thuringiensis* PS43F, and *Bacillus thuringiensis* PS50C, by applying said *Bacillus thuringiensis* isolates to the environment where Scarab pests are known to feed.

3. A process for controlling soil-inhabiting Scarab pests of the family Scarabaeidae which comprises
   (1) preparing a bioinsecticide comprising a *Bacillus thuringiensis* isolate "having all of the identifying characteristics of an isolate" selected from the group consisting of *Bacillus thuringiensis* PS86B1, *Bacillus thuringiensis* PS43F, and *Bacillus thuringiensis* PS50C, or Scarab active mutants thereof, "which retain the parent microbe activity against scarab pests" spores or crystals, thereof; and (2) placing said bioinsecticide on or in the soil or on plants where Scarab pests are feeding.

4. The process, according to claim 3, wherein said bioinsecticide is delivered by a means selected from the group consisting of spray, granules, and polymer to the soil or sub-surface of the soil.

5. The process, according to claims 1 or 3, wherein substantially intact *B.t.* cells, or mutants thereof, are treated to prolong the pesticidal activity when the substantially intact cells are applied to the environment of a Scarab pest.

6. The process, according to claim 5, wherein the application of said bioinsecticide is done upon seed planting or post seed planting of turfgrass.

7. The process, according to claim 1, wherein the Scarab pests are present on stored products.

8. The process, according to claim 1, wherein the Scarab pest is the Masked Chafer, *Cyclocephala sp.*

9. The process, according to claim 1, wherein the Scarab pest is the June Beetle, *Cotinis sp.*

10. The process, according to claim 1, wherein the Scarab pest is the Northern Masked Chafer, *Cyclocephala borealis.*

11. The process, according to claim 1, wherein the Scarab pest is the Japanese Beetle, *Popilla japonica.*

12. The process, according to claim 1, wherein the Scarab pest is the Pasadena Masked Chafer, *Cyclocephala pasadenae.*

* * * * *

UNITED STATES PATENT AND TRADEMARK OFFICE
CERTIFICATE OF CORRECTION

PATENT NO. : 5,185,148  Page 1 of 2

DATED : February 9, 1993

INVENTOR(S) : Tracy E. Michaels

It is certified that error appears in the above-identified patent and that said Letters Patent is hereby corrected as shown below:

Column 2   line 32: "*B.t.* PS86B1, PS50C" should read --*B.t.* PS86B1, *B.t.* PS50C--.

Column 7   line 68: "inactivation of" should read --inactivation or--.

Column 9   line 42: "1 oxz. plastic" should read --1 oz. plastic--.

Column 10  line 27: "such a pUC8" should read --such as pUC8--.

Column 10  lines 47 and 48: Delete all quotation marks (").

Column 10  lines 52 and 53: Delete all quotation marks (").

Column 10  lines 64 and 65: Delete all quotation marks (").

UNITED STATES PATENT AND TRADEMARK OFFICE
CERTIFICATE OF CORRECTION

PATENT NO. : 5,185,148
DATED : February 9, 1993
INVENTOR(S) : Tracy E. Michaels

It is certified that error appears in the above-indentified patent and that said Letters Patent is hereby corrected as shown below:

Column 11, lines 1 and 2, delete all quotation marks (").

Signed and Sealed this

Eighteenth Day of January, 1994

Attest:

BRUCE LEHMAN

Attesting Officer    Commissioner of Patents and Trademarks